United States Patent [19]

Carr et al.

[11] Patent Number: 4,988,826
[45] Date of Patent: Jan. 29, 1991

[54] PROCESS FOR INTERMEDIATES FOR INSECTICIDAL COMPOUNDS

[75] Inventors: Robin A. E. Carr, Little Sandhurst, Nr Camberley; Lyn Powell, Macclesfield, both of United Kingdom

[73] Assignee: Imperial Chemical Industries PLC, London, England

[21] Appl. No.: 411,746

[22] Filed: Sep. 25, 1989

Related U.S. Application Data

[62] Division of Ser. No. 147,868, Jan. 25, 1988, Pat. No. 4,891,450.

[30] Foreign Application Priority Data

Feb. 6, 1987 [GB] United Kingdom ............... 8702717

[51] Int. Cl.$^5$ ........................................... C07D 317/44
[52] U.S. Cl. ................................... 549/445; 549/434; 549/362; 549/350; 568/661; 570/129
[58] Field of Search ............... 549/445, 434, 362, 350; 568/661; 570/129

[56] References Cited

U.S. PATENT DOCUMENTS

| 2,456,316 | 12/1948 | Prill | 549/445 |
| 2,475,423 | 7/1949 | Dickey et al. | 260/74 |
| 3,310,463 | 3/1967 | Hopkins et al. | 549/445 |
| 4,678,811 | 7/1987 | Franke et al. | 514/721 |
| 4,791,123 | 12/1988 | Franke et al. | 549/350 |

FOREIGN PATENT DOCUMENTS

| 0179018 | 4/1986 | European Pat. Off. |
| 0211561 | 2/1987 | European Pat. Off. |
| 0233834 | 8/1987 | European Pat. Off. |
| 0240978 | 10/1987 | European Pat. Off. |
| 1081898 | 5/1960 | Fed. Rep. of Germany. |
| 2178739 | 2/1987 | United Kingdom. |
| 2204582 | 11/1988 | United Kingdom. |

OTHER PUBLICATIONS

Burton et al., *The Journal of Organic Chemistry*, vol. 35, No. 7, pp. 2125-2130 (Jul. 1970).

*Primary Examiner*—Bruce Gray
*Attorney, Agent, or Firm*—Cushman, Darby & Cushman

[57] ABSTRACT

The invention provides novel arylalkene compounds of formula I, a process for their preparation and their use as intermediates for insecticidal compounds, comprising,

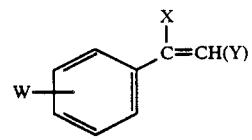

wherein W represents 1 to 4 substituents selected from halo, alkyl, alkoxy, haloalkyl, haloalkoxy and alkoxyalkyl, or W represents a bidentate alkylene or alkylenedioxy group linking adjacent carbon atoms, X represents fluoroalkyl, and Y is selected from chlorine, bromine and alkoxy; and a process for preparing said ethers. The compounds of formula I are prepared by reacting a ketone of formula:

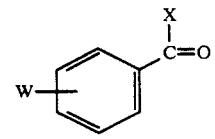

with a phosphonium salt of formula Hal$^-$(Q)$_3$P$^+$—CH$_2$—Y, where Hal$^-$ represents a halide ion and Q represents alkyl or aryl.

3 Claims, No Drawings

PROCESS FOR INTERMEDIATES FOR INSECTICIDAL COMPOUNDS

This is a division of application Ser. No. 07/147,868, filed Jan. 25, 1988, now U.S. Pat. No. 4,891,950.

This invention relates to novel arylalkene derivatives, a process for their preparation and their use as intermediates for the preparation of insecticidal compounds.

In a first aspect, the invention provides a process for preparing a compound of formula I:

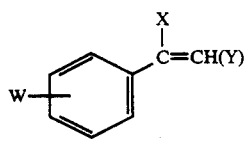

wherein W represents one, two, three or four substituents independently selected from halo, alkyl of up to six carbon atoms, alkoxy of up to six carbon atoms, haloalkyl of up to six carbon atoms, haloalkoxy of up to six carbon atoms and alkoxyalkyl of up to a total of six carbon atoms or W represents a bidentate group linking adjacent carbon atoms selected from alkylene of up to four carbon atoms and alkylenedioxy of up to four carbon atoms, X represents a fluoroalkyl group of up to two carbon atoms, and Y is selected from chlorine, bromine and alkoxy of up to four carbon atoms, which comprises a Wittig reaction between a ketone of formula II:

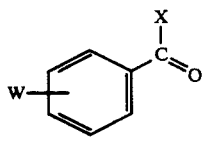

and a phosphonium salt of formula III:

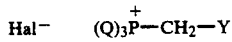

wherein W, X and Y have any of the meanings given hereinabove, Q represents alkyl of up to six carbon atoms or aryl, for example methyl, ethyl or phenyl, and Hal⁻ represents a halide anion, in the presence of a strong base, for example potassium t-butoxide or potassium disilazide.

Particular examples of compounds of formula I which may be prepared by the process of the invention include those wherein W represents one, two or three substituents selected from chloro, bromo, fluoro, methoxy, ethoxy, trifluoromethyl, trifluoromethoxy and difluoromethoxy, X represents trifluoromethyl and Y is selected from chlorine, bromine, methoxy and ethoxy.

Specific examples of the compounds of formula I which may be prepared by the process of the invention include 1,1,1-trifluoro-2-(4-ethoxyphenyl)-3-methoxyprop-2-ene, 1,1,1-trifluoro-2-(4-ethoxyphenyl)-3-chloroprop-2-ene, 1,1,1-trifluoro-2-(4-ethoxyphenyl)-3-bromoprop-2-ene, 1,1,1-trifluoro-2-(4-trifluoromethoxyphenyl)-3-methoxyprop-2-ene, 1,1,1-trifluoro-2-(4-trifluoromethoxyphenyl)-3-chloroprop-2-ene, 1,1,1-trifluoro-2-(4-trifluoromethoxyphenyl)-3-bromoprop-2-ene, 1,1,1-trifluoro-2-(4-trifluoromethylphenyl)-3-methoxyprop-2-ene, 1,1,1-trifluoro-2-(4-trifluoromethylphenyl)-3-chloroprop-2-ene, 1,1,1-trifluoro-2-(4-chlorophenyl)-3-methoxyprop-2-ene, 1,1,1-trifluoro-2-(4-chlorophenyl)-3-chloroprop-2-ene.

In a further aspect the invention provides novel compounds of formula I wherein W, X and Y have any of the meanings given hereinabove. The compounds of formula I wherein Y represents alkoxy are useful as intermediates for the preparation of insecticidally active compounds of formula IV,

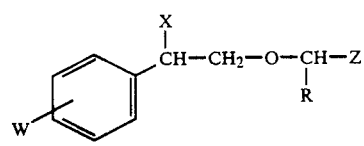

wherein W and X have any of the meanings described hereinabove, Z represents a substituted aryl group where each substituent is selected from halo, alkyl of up to six carbon atoms, aryl, aralkyl of up to six carbon atoms in the alkyl moiety, aryloxy and arylamino and R is selected from hydrogen, cyano, ethynyl, methyl and trifluoromethyl. Examples of compounds of formula IV showing particularly high levels of insecticidal activity include those wherein X represents trifluoromethyl, W represents one, two or three substituents selected from chloro, bromo, fluoro, methoxy, ethoxy, trifluoromethyl, trifluoromethoxy and difluoromethoxy, and Z is an aryl group selected from phenyl, pyridyl and furyl, substituted with one or more substituents selected from fluoro, methyl, phenyl, benzyl, phenoxy, chlorophenoxy, fluorophenoxy, bromophenoxy and fluoroanilino. In a further aspect, therefore, the invention provides a process for the preparation of a compound of formula IV which comprises the steps of:

(i) acid catalysed hydrolysis of a compound of formula I wherein W and X have any of the meanings given hereinabove, and Y represents alkoxy of up to four carbon atoms, thereby producing an aldehyde of formula V:

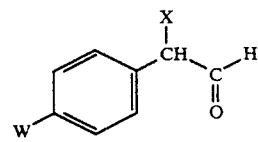

followed by the step of (ii) reduction of the aldehyde of formula V to produce an alcohol of formula VI:

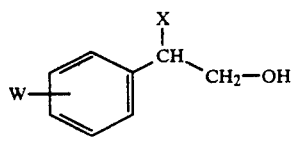

followed by the step of (iii) reaction of the alcohol of formula VI with a compound of formula:

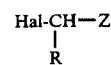

wherein Hal represents a halogen atom and R and Z have any of the meanings described hereinabove, in the presence of a base, optionally in a two-phase system in the presence of a phase transfer catalyst. The compounds of formula I wherein Y represents chlorine or bromine are also useful as intermediates for the preparation of compounds of formula IV. Accordingly, in a yet further aspect, the invention provides a process for the preparation of a compound of formula IV which comprises the step of (i) reaction of a compound of formula I wherein W and X have any of the meanings described hereinabove and Y represents chlorine or bromine with a compound of formula:

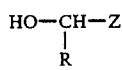

wherein R and Z have any of the meanings described hereinabove, to produce a compound of formula VII:

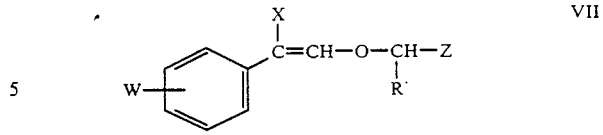

followed by the step of (ii) reduction of the compound of formula VII to produce the compound of formula IV Preferably, the reduction described in step (ii) is performed by hydrogenation in the presence of a suitable catalyst, for example rhodium.

The compounds of formula VII may also be prepared from the compounds of formula I wherein Y is alkoxy by reaction with the alcohol of formula HO-CH(R)-Z in the presence of mercuric acetate, according to the method described in Advanced Organic Chemistry, J. March, 3rd Edition, Page 346 (published by John Wiley and Sons).

The processes described above are summarised by way of example in Scheme 1:

SCHEME 1

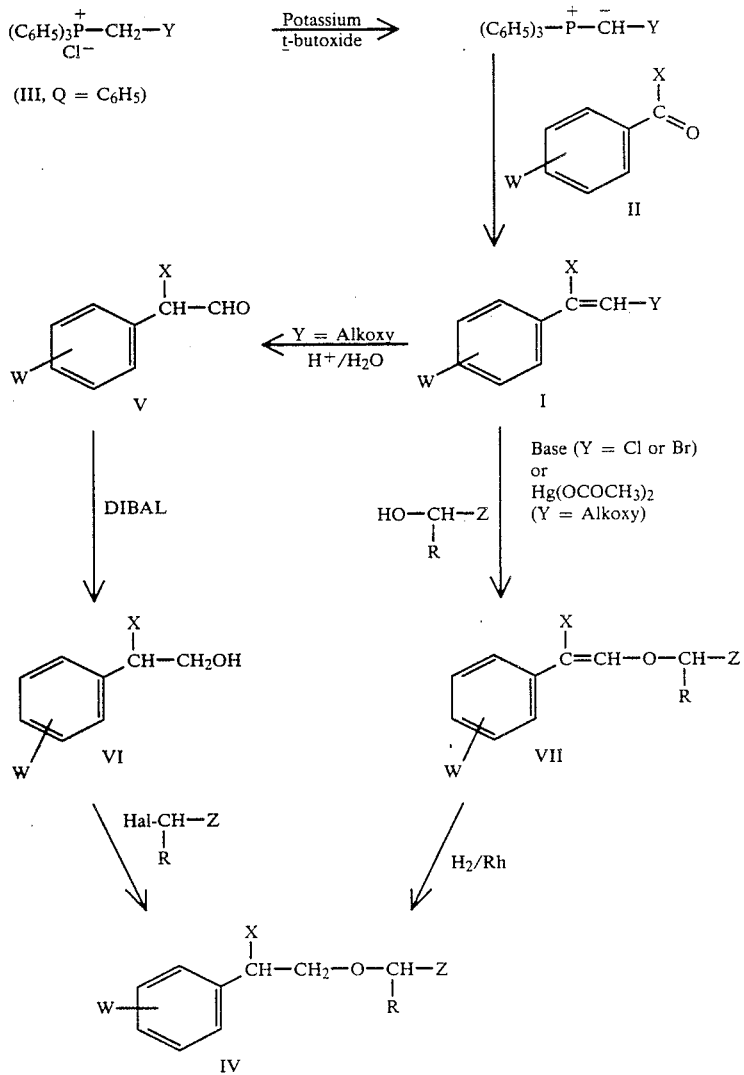

DIBAL = Diisobutylaluminium hydride

Typical examples of the compounds of formula IV which may be prepared by these further processes of the invention are given in Table I. In this table, the compounds correspond to the formula:

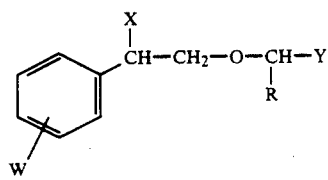

and Y is defined as $R^1$ to $R^{14}$, wherein $R^1$ to $R^{14}$ represent the following groups: $R^1$: 3-phenoxyphenyl $R^2$: 3-(4-chlorophenoxy)phenyl $R^3$: 4-fluoro-3-phenoxyphenyl $R^4$: 3-(4-bromophenoxy)phenyl $R^5$: 4-fluoro-3-(4-bromophenoxy)phenyl $R^6$: 4-fluoro-3-(4-chlorophenoxy)phenyl $R^7$: 3-(2,4-difluorophenoxy)phenyl $R^8$: 3-benzylphenyl $R^9$: 3-benzyl-4-fluorophenyl $R^{10}$: 3-(4-fluorophenylamino)phenyl $R^{11}$: 6-phenoxypyrid-2-yl $R^{12}$: 2-methyl-3-phenylphenyl $R^{13}$: 4-methyl-2,3,5,6-tetrafluorophenyl $R^{14}$: 5-benzylfuran-3-yl

TABLE I

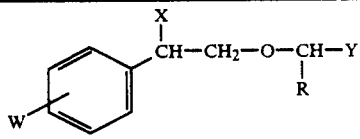

| COMPOUND NO | W | X | R | Y |
|---|---|---|---|---|
| 1 | 4-OC$_2$H$_5$ | CF$_3$ | H | R$^1$ |
| 2 | 4-OC$_2$H$_5$ | CF$_3$ | H | R$^{13}$ |
| 3 | 4-OC$_2$H$_5$ | CF$_3$ | H | R$^2$ |
| 4 | 4-OC$_2$H$_5$ | CF$_3$ | H | R$^{11}$ |
| 5 | 4-OC$_2$H$_5$ | CF$_3$ | H | R$^6$ |
| 6 | 4-OC$_2$H$_5$ | CF$_3$ | H | R$^5$ |
| 7 | 4-OC$_2$H$_5$ | CF$_3$ | H | R$^{12}$ |
| 8 | 4-OC$_2$H$_5$ | CF$_3$ | H | R$^9$ |
| 9 | 4-OC$_2$H$_5$ | CF$_3$ | H | R$^4$ |
| 10 | 4-OC$_2$H$_5$ | CF$_3$ | H | R$^7$ |
| 11 | 4-OC$_2$H$_5$ | CF$_3$ | H | R$^{10}$ |
| 12 | 4-OC$_2$H$_5$ | CF$_3$ | H | R$^8$ |
| 13 | 3-F, 4-OC$_2$H$_5$ | CF$_3$ | H | R$^2$ |
| 14 | 3-F, 4-OC$_2$H$_5$ | CF$_3$ | H | R$^1$ |
| 15 | 4-Cl | CF$_3$ | H | R$^3$ |
| 16 | 4-Cl | CF$_3$ | H | R$^1$ |
| 17 | 2,4-Cl$_2$ | CF$_3$ | H | R$^1$ |
| 18 | 4-F | CF$_3$ | H | R$^3$ |
| 19 | 3,4-(CF$_2$)$_3$ | CF$_3$ | H | R$^3$ |
| 20 | 4-(CF$_2$)$_2$CF$_3$ | CF$_3$ | H | R$^3$ |
| 21 | 4-C(CF$_3$)$_3$ | CF$_3$ | H | R$^3$ |
| 22 | 4-CF$_3$ | CF$_3$ | H | R$^1$ |
| 23 | 4-CF$_2$OCF$_3$ | CF$_3$ | H | R$^2$ |
| 24 | 4-CF$_2$OCF$_3$ | CF$_3$ | H | R$^1$ |
| 25 | 4-OCF$_3$ | CF$_3$ | H | R$^3$ |
| 26 | 4-OCF$_3$ | CF$_3$ | H | R$^2$ |
| 27 | 4-OCF$_3$ | CF$_3$ | H | R$^1$ |
| 28 | 4-OCF$_3$ | CF$_3$ | H | R$^{11}$ |
| 29 | 4-OCF$_3$ | CF$_3$ | H | R$^6$ |
| 30 | 4-OCF$_3$ | CF$_3$ | H | R$^8$ |
| 31 | 4-OCF$_3$ | CF$_3$ | H | R$^9$ |
| 32 | 4-OCF$_3$ | CF$_3$ | H | R$^{10}$ |
| 33 | 4-OCF$_3$ | CF$_3$ | H | R$^3$ |
| 34 | 4-OCF$_3$ | CF$_3$ | H | R$^1$ |
| 35 | 3,4-(OCF$_2$O) | CF$_3$ | H | R$^1$ |
| 36 | 3,4-(OCF$_2$O) | CF$_3$ | H | R$^2$ |
| 37 | 4-OC$_2$H$_5$ | CF$_3$ | H | R$^3$ |
| 38 | 4-CF$_3$ | CF$_3$ | H | R$^3$ |
| 39 | 4-CF$_3$ | CF$_3$ | H | R$^1$ |
| 40 | 4-CF$_3$ | CF$_3$ | H | R$^6$ |
| 41 | 4-CF$_3$ | CF$_3$ | H | R$^8$ |
| 42 | 4-CF$_3$ | CF$_3$ | H | R$^{10}$ |
| 43 | 4-CF$_3$ | CF$_3$ | H | R$^{11}$ |
| 44 | 4-CF$_3$ | CF$_3$ | H | R$^9$ |

TABLE I-continued

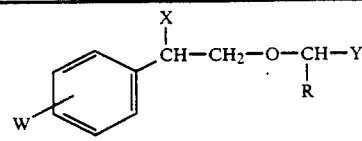

| COMPOUND NO | W | X | R | Y |
|---|---|---|---|---|
| 45 | 4-OCHF$_2$ | CF$_3$ | H | R$^2$ |
| 46 | 4-OCHF$_2$ | CF$_3$ | H | R$^1$ |
| 47 | 4-OCHF$_2$ | CF$_3$ | H | R$^3$ |
| 48 | 4-OC$_2$H$_5$ | CF$_3$ | CF$_3$ | R$^1$ |
| 49 | 4-OC$_2$H$_5$ | CF$_3$ | CF$_3$ | R$^3$ |
| 50 | 4-OC$_2$H$_5$ | CF$_3$ | CF$_3$ | R$^2$ |
| 51 | 4-OC$_2$H$_5$ | CF$_3$ | CF$_3$ | R$^6$ |
| 52 | 4-OCF$_3$ | CF$_3$ | CF$_3$ | R$^6$ |
| 53 | 4-OCF$_3$ | CF$_3$ | CF$_3$ | R$^1$ |
| 54 | 4-OCF$_3$ | CF$_3$ | CF$_3$ | R$^2$ |
| 55 | 4-OCF$_3$ | CF$_3$ | CF$_3$ | R$^3$ |
| 56 | 4-OC$_2$H$_5$ | CF$_3$ | CF$_3$ | R$^1$ |
| 57 | 4-OC$_2$H$_5$ | CF$_3$ | CF$_3$ | R$^2$ |
| 58 | 4-OC$_2$H$_5$ | CF$_3$ | CF$_3$ | R$^6$ |
| 59 | 4-OC$_2$H$_5$ | CF$_3$ | CF$_3$ | R$^3$ |
| 60 | 4-CF$_3$ | CF$_3$ | H | R$^2$ |
| 61 | 4-OCHF$_2$ | CF$_3$ | H | R$^6$ |
| 62 | 4-OCHF$_2$ | CF$_3$ | H | R$^8$ |
| 63 | 4-OCHF$_2$ | CF$_3$ | H | R$^9$ |
| 64 | 4-OCHF$_2$ | CF$_3$ | H | R$^{10}$ |
| 65 | 4-OCHF$_2$ | CF$_3$ | H | R$^{11}$ |
| 66 | 4-OC$_2$H$_5$ | CF$_3$ | CN | R$^1$ |
| 67 | 4-OC$_2$H$_5$ | CF$_3$ | C≡CF | R$^1$ |
| 68 | 4-OC$_2$H$_5$ | CF$_3$ | C≡CF | R$^3$ |
| 69 | 4-Cl | CF$_3$ | H | R$^2$ |
| 70 | 4-Cl | CF$_3$ | H | R$^6$ |

Specific examples of compounds according to formula IV which may be prepared by the processes described herein include 1,1,1-trifluoro-2-(4-ethoxyphenyl)-3-(3-phenoxybenzyloxy)propane, 1,1,1-trifluoro-2-(4-ethoxyphenyl)-3-[3-(4-chlorophenoxy)benzyloxy]propane, 1,1,1-trifluoro-2-(4-ethoxyphenyl)-3-[3-(4-chlorophenoxy)-4-fluorobenzyloxy]propane, 1,1,1-trifluoro-2-(4-chlorophenyl)-3-[3-(4-chlorophenoxy)benzyloxy]propane, 1,1,1-trifluoro-2-(4-chlorophenyl)-3-(3-phenoxybenzyloxy)propane, 1,1,1-trifluoro-2-(4-trifluoromethylphenyl)-3-(3-phenoxybenzyloxy)propane and 1,1,1-trifluoro-2-(4-trifluoromethylphenyl)-3-(4-fluoro-3-phenoxybenzyloxy)propane.

Some of the compounds represented by the formula IV are disclosed in the applicant's copending UK patent application Ser. No. 2178739. Others have not been specifically described before. Accordingly, in a further aspect, the invention provides the following compound: 1,1,1-trifluoro-2-(4-trifluoromethoxyphenyl)-3-[3-(4-chlorophenoxy)-4-fluorobenzyloxy]propane.

The compounds of formula IV may exist in alternative isomeric forms due to asymmetric substitution at one or, depending on the value of R, two carbon atoms. It is to be understood that the invention includes within its scope not only isomer mixtures (including racemates) but also any single isomer of an invention compound in isolation or substantially free from any other isomer.

Further details concerning the preparation and characterisation of the compounds of the invention are given hereinafter in the Examples.

The compounds of formula (IV) may be used to combat and control infestations of insect and acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (IV) suitable inert diluent or carrier materials, and/or surface active agents.

The compounds of the invention may be the sole active ingredient of the composition or they may be admixed with one or more additional active ingredients such as insecticides, insecticide synergist, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrins, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, dichlorvos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion and diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones and synthetic mimics thereof such as juvenile hormone, juvabione, ecdysones, methoprene and hydroprene.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides or acaricides specific for particular insect species/stages for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips, sprays or aerosols. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosine and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 1-99% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of formula (IV) and compositions comprising them are very toxic to wide varieties of insect, acarine and other invertebrate pests, including, for example, the following:

*Myzus persicae* (aphids)
*Aphis fabae* (aphids)
*Megoura viceae* (aphids)
*Aedes aegypti* (mosquitos)
*Anopheles* spp. (mosquitos)
*Culex* spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Aonidiella* spp. (scale insects)
*Trialeuroides* spp. (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
*Diabrotica* spp. (rootworms)
*Agrotis* spp. (cutworms)
*Chilo partellus* (maize stem borers)
*Nilaparvata lugens* (plant hoppers)
*Nephotettix cincticeps* (leaf hoppers)
*Panonychus ulmi*
*Panonychus citri*
*Tetranychus urticae* (red spider mite)
*Tetranychus cinnabarinus* (carmine spider mite)

The compounds according to formula (IV) and compositions comprising them have been shown to be useful for the control of lepidopteran pests, for example *Spodoptera* spp. and *Heliothis* spp. and public health pests such as flies, mosquitos and cockroaches. They are particularly useful for the control of acarine pests such as *Tetranychus* spp. and *Panonychus* spp. and pests of maize and rice such as *Chilo* spp. (stem borers), *Nilaparvata* spp. and *Nephotettix* spp. (plant and leaf hoppers). Some of the compounds are of particular value for the control of pests of rice because they show high levels of activity against these pests at rates which are not toxic to fish, thus enabling their use in paddy rice where fish are cultivated in the paddy. They may also be useful in combating insect and acarine pests which infest domestic animals, such as *Lucilia sericata*, and ixodid ticks such as *Boophilus* spp., *Ixodes* spp., *Amblyomma* spp., *Rhipicephalus* spp. and *Dermocentor* spp. They are effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic reasonance (NMR) spectroscopy and infra red (IR) spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak, CPSil 5CB column of 12.5M length and 0.2 mm internal diameter. Unless otherwise stated, the injection temperature was 100° C., and a temperature gradient of 15° C./minute employed, up to a maximum temperature of 250° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270MHz on a Jeol FX 270 NMR spectrometer, unless otherwise indicated. 90 MHz, 60 MHz, and 400 MHz $^1$H NMR spectrometry were performed using Jeol FX 90Q, Jeol PMX 60SI, and Jeol GX400 spectrometers respectively.

$^9$F NMR spectrometry was performed on a Jeol FX90Q spectrometer at a frequency of 84.26 MHz. All NMR shift ($\delta$) values are quoted in ppm relative to a standard (TMS or CFCl$_3$).

Molecular Ion (M$^+$) peaks were determined on one of three mass spectrometers : Jeol DX303, Kratos MS80 or Hewlett Packard HP 5992.

The following Examples illustrates various aspects of the invention.

EXAMPLE 1

This Example illustrates the preparation of 4-bromo-α,α,α-trifluoroacetophenone.

Literature reference: Journal of Organometallic Chemistry, 251, 139–48, (1983).

A mixture of 1,4-dibromobenzene (64g), dry tetrahydrofuran (600 cm$^3$) and dry diethyl ether (600 cm$^3$) was cooled to −78° C. under an atmosphere of nitrogen. n-Butyllithium (108.4 cm$^3$ of a 2.5 molar solution in hexane) was added to the stirred mixture over 40 minutes, the temperature of the reaction mixture being maintained below −72° C. by external cooling; the mixture was then stirred for a further 40 minutes. Methyl trifluoroacetate (35.4g) was then added over 40 minutes, and stirring continued for a further 30 minutes, the temperature being maintained below −68° C. throughout. The reaction mixture was then carefully quenched by adding a mixture of concentrated hydrochloric acid (60 cm$^3$) and ethanol (40cm$^3$), precooled to −78° C., over a period of 10 minutes. After stirring for a further 20 minutes, the reaction mixture was allowed to warm to the ambient temperature (ca. 22° C.). The organic layer was separated and concentrated by evaporation under reduced pressure to leave a water-contaminated oil (70g). The oil was dissolved in diethyl ether, and the solution dried over anhydrous magnesium sulphate. Evaporation of the solvent under reduced pressure gave an orange oil, which was purified by distillation under reduced pressure (ca. 15 mm Hg). Two fractions containing essentially the same material, 4-bromo-α,α,α-trifluoroacetophenone, were obtained. The first fraction (17.19g), boiling within a range of 78–83° C., was shown to be 85% pure by gas liquid chromatography; the second fraction (41.13g), boiling range 83–84° C., was shown to be 99% pure by gas liquid chromatography. The second fraction crystallised on standing.

$^1$H NMR (CDCl$_3$)δ(ppm): 7.7(2H,m); 7.95(2H,m).

$^{19}$F NMR (CDCl$_3$)δ(ppm)–relative to CFCl$_3$: −72.1.

EXAMPLE 2

4-Trifluoromethoxy-α,α,α-trifluoroacetophenone was prepared from 4-bromotrifluoromethoxybenzene by a procedure similar to that described in Example 1.

4-Bromotrifluoromethoxybenzene may be prepared from trifluoromethoxybenzene by the process described in the Journal of Organic Chemistry, 29, 1, (1964).

Boiling point : 164–166° C. (atmosphere pressure).

$^1$H NMR (CDCl$_3$)δ(ppm): 7.35, 8.14(4H,d).

$^{19}$H NMR (CDCl$_3$)δ(ppm relative to CFCl$_3$): −58.1(s)CF$_3$O; −72.1(s)CF$_3$.

GLC retention time: 1.50minutes (50° C. -280° C. run).

EXAMPLE 3

This Example illustrates the preparation of EZ-1,1,1,-trifluoro-2-(4-ethoxyphenyl)-3-methoxyprop-2-ene.

Potassium t-butoxide (5.2 g) was added to a stirred suspension of (methoxymethyl)triphenylphosphonium chloride (15 g) in dry diethyl ether (50 cm$^3$) under an atmosphere of nitrogen. The suspension was stirred for 30 minutes at the ambient temperature (ca 20° C.) to allow formation of the ylid, and the resultant solution was then added dropwise to a solution of α,α,α-trifluoro-4-ethoxyacetophenone (3 g) in dry diethyl ether (25 cm$^3$). The reaction mixture was heated at the reflux temperature for 3 hours. After cooling, the mixture was filtered through celite and washed With Water (3×10 cm$^3$). The solvent was evaporated under reduced pressure, and the residual oil was purified by flash chromatography on silica gel, eluting firstly with n-hexane, and secondly n-hexane containing (10% by volume diethyl ether, to give EZ-1,1,1-trifluoro-2-(4-ethoxyphenyl)-3-methoxyprop-2-ene (2.9 g).

90 MHZ $^1$H NMRδ(CDCl$_3$)(ppm): 1.4(3H,t); 3.75–3.80(3H, 2s at 1:1 ratio), 4.0(2H,q); 6.35(0.5H,s); 7.15(0.5H,s); 6.8–7.4(4H,m).

E:Z isomer ratio approx 1:1.

EXAMPLE 4

The following compounds were prepared by a process analogous to that described in Example 3.

(i) E,Z-1,1,1-Trifluoro-2-(4-trifluoromethylphenyl)-3-methoxyprop-2-ene. (Prepared in 50% purity)

60 MHz $^1$H NMR (CDCl$_3$)δ(ppm): 3.9(3H,s); 6.5(1H,s); 6.9–7.4(4H,m).

(ii) E,Z-1,1,1-trifluoro-2-(4-trifluoromethoxyphenyl)-3-methoxyprop-2-ene

60 MHz $^1$H NMR (CDCl$_3$)δ(ppm): 3.9(3H,s); 6.4(1H,s); 7.1–7.4(4H,m).

EXAMPLE 5

This Example illustrates the two stage procedure for the preparation of (RS)-1,1,1-trifluoro-2-(4-ethoxyphenyl)propan-3-ol.

Stage 1

Preparation of (RS)-1,1-trifluoro-2-(4 -ethoxyphenyl)propanal.

1,1,1-Trifluoro-2-(4-ethoxyphenyl)-3-methoxyprop-2-ene (3.1 g) was treated with a solution of concentratrated sulphuric acid (8 g) and water (4.4 cm$^3$). The resulting solution was stirred at 60–75° C. for 6 hours. After cooling, the solution was neutralised with solid sodium hydrogen carbonate and diethyl ether (40 cm$^3$) and water (40 cm$^3$) were added to the resulting slurry. The mixture was partitioned, and the aqueous layer was further extracted with diethyl ether (3×40 cm$^3$). The combined organic layers were combined, dried over anhydrous sodium sulphate and the solvent evaporated under reduced pressure to give (RS)-1,1,1-trifluoro-2-(4-ethoxyphenyl)propanal as an oil, which was used without further purification.

Stage 2

The crude aldehyde from stage 1 was dissolved in dry toluene (15 cm$^3$) and treated with excess di-isobutyl aluminium hydride (25 cm$^3$ of a 1 molar solution in toluene) at a temperature maintained at −78° C. The reaction mixture was stirred for 20 minutes, then quenched with water (80 cm$^3$) and acetic acid (1.5 cm$^3$). Diethyl ether (50 cm$^3$) was added and the mixture was allowed to warm to the ambient temperature. Dilute aqueous hydrochloric acid solution was added until all aluminium salts had dissolved, and the mixture was separated. The aqueous layers were further extracted with diethyl ether, and the organic layers were dried over anhydrous sodium sulphate and the solvent evaporated under reduced pressure to give an oil. The oil was purified by flash column chromatography on silica gel, using petroleum ether containing a gradually increased proportion (10–40% by volume) of diethyl ether as eluent, to give (RS)-1,1,1-trifluoro-2-(4-ethoxyphenyl)-propan-3-ol (2.2 g).

Infra red (liquid film): 3400(broad), 1620, 1520, 1310, 1255, 1166, 1120, 1050 cm$^{-1}$.

EXAMPLE 6

The following compounds were prepared by a two stage procedure analogous to that described in Example 5.

(i) (RS)-1,1,1-trifluoro-2-(4-trifluoromethylphenyl)-propan-3-ol.

$^1$H NMR (CDCl$_3$)δ(ppm): 1.9(1H,bs); 3.5(1H,m); 4.0(2H,m); 7.2–7.8(4H,m).

(ii) (RS)-1,1,1-trifluoro-2-(4-trifluoromethoxyphenyl)propan-3-ol.

$^1$H NMR (CDCl$_3$)δ(ppm): 1.9(1H,bs); 3.5(1H,m); 4.0(2H,m); 7.2–7.4(4H,m).

EXAMPLE 7

This Example illustrates the preparation of (RS)-1,1,1-trifluoro-2-(4-ethoxyphenyl)-3-[3-(4-chlorophenoxy)benzyloxy]propane (Compound No 3).

Triethylamine (1,1 g) followed by mesyl chloride (0.08 g) was added to a stirred solution of 3-(4-chlorophenoxy)benzyl alcohol (1.5 g) in dichloromethane (1.5 g) at 0° C. After 5 minutes, the reaction mixture was allowed to warm to the ambient temperature (ca 25° C.). After a further 30 minutes, diethyl ether (30 cm$^3$) was added and the reaction mixture was filtered through celite.

The solvents were evaporated under reduced pressure and the resultant crude mesylate was dissolved in dichloromethane (20 cm$^3$). (RS)-1,1,1-Trifluoro-2-(4-ethoxyphenyl) propan-3-ol (1 g), tetra-n-butylammonium hydrogen sulphate (0.05 g) and 40% aqueous sodium hydroxide solution (10 cm$^3$) were added, and the mixture was stirred at the ambient temperature for 6 hours.

The mixture was diluted with water (20 cm$^3$), and the product extracted into dichloromethane (3×20 cm$^3$). The combined organic layers were dried over ahydrous sodium sulphate, and the solvent evaporated under reduced pressure. The residual oil was purified by flash column chromatography on a silica gel support, eluting with petroleum ether containing a gradually increased proportion (5–10% by volume) of diethyl ether to give (RS)-1,1,1-trifluoro-2-(4-ethoxyphenyl)-3-[3-(4-chlorophenoxy)benzyloxy]propane (1.2 g).

$^1$H NMR (CDCl$_3$)δ(ppm): 1.41(3H,t); 3.56(1H,m); 3.80(1H,t); 3.9–4.1(2H,q) overlapping with (1H,dd); 4.48(2H,ABq); 6.8–7.4(12H,m).

$^{19}$F NMR (CDCl$_3$)δ(ppm–relative to CFCl$_3$): −68.4(CF$_3$, d).

GLC retention time: 11.92 minutes.

EXAMPLE 8

The following compounds were prepared from the appropriate starting materials by a procedure similar to that described in Example 7.

(i) (RS)-1,1,1-Trifluoro-2-(4-trifluoromethoxyphenyl)-3-[3-(4-chlorophenoxy)-4-fluorobenzyloxy]-propane (Compound No 29) from (RS)-1,1,1-trifluoro-2-(4-trifluoromethoxy)propan-3-ol and 3-(4-chlorophenoxy)-4-fluorobenzyl alcohol.

(Product purified by analytical high pressure liquid chromatography on a silica gel column, eluted with n-hexane containing 20% by volume dichloromethane).

$^1$H NMR (CDCl$_3$)δ(ppm): 3.65(1H,m); 3.8(1H,dd); 3.96(1H,dd); 4.42(2H,ABq); 6.85–7.4(11H,m).

$^{19}$H NMR (CDCl$_3$)δ(ppm relative to CFcl$_3$): −58,4(3F,s); −68.2(3F,d,J=8.4Hz); −132.2(1F,m).

(ii) (RS)-1,1,1-Trifluoro-2-(4-trifluoromethylphenyl)-3-(3-phenoxybenzyloxy)propane (Compound No 39), from (RS)-1,1,1-trifluoro-2-(4-trifluoromethylphenyl)-propan-3-ol and 3-phenoxybenzyl alcohol.

(Product purified by column chromatography on silica gel, eluted with n-hexane containing a gradually increasing proportion (10–20% by volume) of diethyl ether).

$^1$H NMR (CDCl$_3$)(ppm): 3.65(1H,m); 3.8(1H,dd); 3.96(1H,dd); 4.35(2H,ABq); 6.80–7.50(13H,m).

(iii) (RS)-1,1,1-Trifluoro-2-(4-trifluoromethylphenyl)-3-(3-phenoxy-4-fluorobenzyloxy)propane (Compound No 38), from (RS)-1,1,1-trifluoro-2-(4-trifluoromethylphenyl)propan-3-ol and 3-phenoxy-4-fluorobenzyl alcohol.

(Product purified as in Example 8 (ii) above).

$^1$H NMR (CDCl$_3$)δ(ppm): 3.65(1H,m); 3.8(1H,dd); 3.96(1H,dd); 4.35(2H,ABq); 6.8–7.5(12H,m).

EXAMPLE 9

This Example illustrates the preparation of EZ-1,1,1-trifluoro-2-(4-ethoxyphenyl)-3-chloroprop-2-ene.

Potassium disilazide (76 cm$^3$ of a 1M solution in tetrahydrofuran) was added slowly to a stirred solution of (chloromethyl)triphenylphosphonium chloride (27 g) in dry tetrahydrofuran (100 cm$^3$) at 0° C. The solution was stirred for 30 minutes to allow formation of the ylid, then added to a solution of α,α,α-trifluoro-4-ethoxyacetophenone (15 g) in tetrahydrofuran (20 cm$^3$) at 0° C. After warming to the ambient temperature, the reaction mixture was poured into water (100 cm$^3$) and the product extracted into diethyl ether (3×50 cm$^3$). The combined organic layers were dried over anhydrous sodium sulphate, and the solvent evaporated. The crude residue was purified by column chromatography on a silica gel support, eluted with n-hexane containing 3% by volume diethyl ether, to give EZ-1,1,1-trifluoro-2-(4-ethoxyphenyl)-3-chloroprop-2-ene (3.5 g).

$^1$H NMR (CDCl$_3$)δ(ppm): 1.4(3H,t); 4.05(2H,q); 6.9(2H,d); 7.05(1H,m); 7.3(2H,d).

E:Z isomer ration approx 1:1

EXAMPLE 10

EZ-1,1,1-Trifluoro-2-(4-trifluoromethoxyphenyl)-3-chloroprop-2-ene was prepared by a procedure analogous to that described in Example 9.

$^1$H NMR (CDCl$_3$)δ(ppm): 6.5(0.33H,s); 7.18(0.67H,broad s); 7.2–7.4(4H,m).

EXAMPLE 11

This Example illustrates the preparation of 1,1,1-trifluoro-2-(4-ethoxyphenyl)-3-[3-(4-chlorophenoxy)-4-fluorobenzyloxy]prop-2-ene.

A solution of 3-(4-chlorophenoxy)-4-fluorobenzyl alcohol (6.3 g) in N,N-dimethylformamide (20 cm$^3$) was added to a stirred suspension of sodium hydride (1.2 g of a 50% dispersion in oil) in N,N-dimethylformamide. After 30 minutes, this mixture was added to a stirred solution of EZ-1,1,1-trifluoro-2-(4-ethoxyphenyl)-3-chloroprop-2-ene (5 g) in N,N-dimethylformamide (25 cm$^3$) at a temperature maintained at −10° C. during the addition. After 45 minutes the reaction mixture was poured into water (150cm$^3$) and sodium chloride added. The products were extracted into diethyl ether (4×100 cm$^3$), and the combined organic layers were dried over anhydrous sodium sulphate and concentrated by evaporation under reduced pressure. The crude residue was purified by column chromatography on a silica gel support, eluted with n-hexane containing 6% by volume diethyl ether, to give 1,1,1-trifluoro-2-(4-ethoxyphenyl)-3-[3-(4-chlorophenoxy)-4-fluorobenzyloxy]-prop-2-ene (6 g).

$^1$H NMR (CDCl$_3$)δ(ppm): 1.4(3H,t); 4.0(2H,q); 4.9(2H,s); 6.8–7.4(12H,m).

EXAMPLE 12

This Example illustrates the preparation of (RS)-1,1,1-trifluoro-2-(4-ethoxyphenyl)-3-[3-(4-chlorophenoxy)4-fluorobenzyloxy]propane (Compound No 5).

A mixture of 1,1,1-trifluoro-2-(4-ethoxyphenyl)-3-[3-(4-chlorophenoxy)-4-fluorobenzyloxy]prop-2-ene (6 g), rhodium on alumina (0.45 g - commercially available from the Aldrich Chemical Company Ltd, The old Brickyard, New Road, Gillingham, Dorset, England) and ethanol (130 cm$^3$) was stirred under hydrogen at a pressure of 3.2 atmospheres for 8 hours. The catalyst was removed by filtration and the solvent evaporated under reduced pressure. The residual oil was purified by column chromatography on a silica gel support, eluted with n-hexane containing 30% by volume dichloromethane, to give (RS)-1,1,1-trifluoro-2-(4-ethoxyphenyl)-3-[3-(4-chlorophenoxy)-4-fluorobenzyloxy]-propane.

$^1$H NMR (CDCl$_3$)δ(ppm): 1.42(3H,t); 3.56(1H,m); 3.78(1H,t); 3.95(1H,dd) overlapping with 4.02(2H,q); 4.4(2H,ABq); 6.8–7.3(11H,m).

$^{19}$H NMR (CDCl$_3$)δ(ppm-relative to CFCl$_3$): −68.4(CF$_3$,d); −132.4(1F,m).

GLC retention time: 11.91 minutes

EXAMPLE 13

This Example illustrates the insecticidal properties of the Products of formula IV according to this invention.

The activity of the Product was determined using a variety of insect pests. The Product was used in the form of liquid preparations containing from 100 to 500 parts per million (ppm) by weight of the Product. The preparations were made by dissolving the Product in acetone and diluting the solutions with water containing 0.1% by weight of a wetting agent sold under the trade name "SYNPERONIC" NX until the liquid preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

In the case of the species *Musca domestica* (housefly), an additional assessment to determine the knockdown effect of the compounds was performed. Details are given in Table II.

The results of the tests are given in Table III for each of the Products, at the rate in parts per million given in the second column as a grading of mortality designated as A, B or C wherein A indicates 80–100% mortality or knockdown, B indicates 50–79% mortality knockdown or knockdown and C indicates less than 50% mortality or knockdown.

In Table III the pest organism used is designated by a letter code and the pests species, the support medium or food, and the type and duration of test is given in Table II.

TABLE II

| CODE LETTERS (Table IV) | TEST SPECIES | SUPPORT MEDIUM/FOOD | TYPE OF TEST | DURATION (days) |
|---|---|---|---|---|
| TUa | *Tetranychus urticae* (spider mites - adult) | French bean leaf | Contact | 3 |
| TUe | *Tetranychus urticae* (spider mites - ova) | French bean leaf | Contact | 6 |
| MP | *Myzus persicae* (aphids) | Chinese Cabbage leaf | Contact | 3 |
| NL | *Nilaparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| MD/KD | *Musca domestica* (houseflies - adults) | Cotton/wool sugar | Knockdown | 4 hours |
| SP | *Spodoptera exigua* (lesser army worm - larvae) | Cotton leaf | Residual | 3 |

"Contact" test indicates that both pests and medium were treated and "residual" indicates that the medium was treated before infestation with the pests.

TABLE III

| COMPOUND | RATE | TuA | TuE | MP | NL | MD/KD | MD | BG | HV | SP | DB |
|---|---|---|---|---|---|---|---|---|---|---|---|
| 3 | 250 | C | — | A | A | A | A | A | C | — | A |
| 5 | 500 | B | — | A | A | A | A | A | A | — | A |
| 29 | 500 | A | A | A | A | A | A | A | A | A | A |
| 38 | 500 | A | A | A | A | A | A | A | A | A | A |

TABLE III-continued

| COMPOUND | RATE | TuA | TuE | MP | NL | MD/KD | MD | BG | HV | SP | DB |
|---|---|---|---|---|---|---|---|---|---|---|---|
| 39 | 500 | C | A | A | A | A | A | A | A | A | A |

We claim:

1. A compound of the formula:

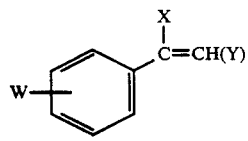

wherein W represents a bidentate group linking adjacent carbon atoms selected from alkylene of up to four carbon atoms and alkylenedioxy of up to four carbon atoms, X represents a fluoroalkyl group of up to two carbon atoms, and Y is selected from chlorine, bromine and alkoxy.

2. A compound according to claim 1 wherein W is alkylenedioxy of up to four carbons.

3. A compound according to claim 2 wherein W is 3,4-($OCH_2O$), X is $CF_3$ and Y is methoxy.

* * * * *